United States Patent [19]
Dow

[11] Patent Number: 6,001,856
[45] Date of Patent: *Dec. 14, 1999

[54] β-ADRENERGIC AGONISTS TO REDUCE A WASTING CONDITION

[75] Inventor: Robert L. Dow, Waterford, Conn.

[73] Assignee: Pfizer Inc., New York, N.Y.

[*] Notice: This patent is subject to a terminal disclaimer.

[21] Appl. No.: 09/033,263

[22] Filed: Mar. 2, 1998

Related U.S. Application Data

[60] Provisional application No. 60/049,584, Jun. 13, 1997.

[51] Int. Cl.⁶ ...................... C07D 211/70; C07D 213/73; A01N 43/40
[52] U.S. Cl. .......................... 514/330; 514/312; 514/313; 514/318; 514/331; 546/300; 546/304; 546/311
[58] Field of Search ................................ 514/89, 90, 183, 514/312, 313, 318, 331, 330; 546/191, 194, 300, 304, 311

[56] References Cited

U.S. PATENT DOCUMENTS

| | | | |
|---|---|---|---|
| 4,358,455 | 11/1982 | Atkinson et al. | 424/263 |
| 5,561,142 | 10/1996 | Fisher et al. | 514/312 |
| 5,597,843 | 1/1997 | Girten et al. | 514/376 |
| 5,714,506 | 2/1998 | Fisher et al. | 514/352 |

FOREIGN PATENT DOCUMENTS

| | | | |
|---|---|---|---|
| WO9635670 | 11/1996 | WIPO | C07D 213/73 |
| WO9635671 | 11/1996 | WIPO | C07D 213/73 |

OTHER PUBLICATIONS

Krief, Stephanie, et al., J. Clin. Invest. vol. 91, Jan. 1993, pp. 344–349, "Tissue Distribution of β3–adrenergic Receptor mRNA in Man".

Simiand, Jacques, et al., European Journal of Pharmacology vol. 219 (1992), pp. 193–201, "Antidepressant profile in rodents of SR 58611A, a new selective agonist for atypical β–andrenoceptors".

Giudice, Antonina, et al, Life Sciences, vol. 44, (19), (1989), pp. 1411–1417, "Inhibition of Rat Colonic Motility and Cardiovascular Effects of New Gut–Specific Bata–Adrenergic Phenylethanolominotetralines".

Tesfamariam, Belay, et al., Br. J. Pharmacol. (1994), 112, pp. 55–58, "$β_1$–and $β_2$–adrenoceptor antagonist activities of ICI–215001,a putative $β_3$–adrenoceptor agonist".

Martin, Corinne A.E., et al., Br. J. Pharmacol. (1993), 110, pp. 1311–1316, "Effects of two $β_3$–adrenoceptor agonists, SR 58611A and BRL 37344, and of salbutamol on cholinergic and NANC neural contraction in guinea–pig main bronchi in vitro".

Taneja, D.T., et al., J. Pharm and Exp. Therapeutics, vol. 260, 1, (1992), pp. 192–200, "Evidence for a Noradrenergic Innervation to "Atypical" Beta Adrenoceptors (or Putative Beta–3 Adrenoceptors) in the Ileum of Guinea Pig [1]".

Kim, Yong S., et al., Life Sciences, vol. 50, pp. 397–407, "Minireview—β–Adrenergic Agonists and Hypertrophy of Skeletal Muscles [1]" (1992).

*Primary Examiner*—Ralph Gitomer
*Assistant Examiner*—Marjorie A. Moran
*Attorney, Agent, or Firm*—Peter C. Richardson; Gregg C. Benson; A. Dean Olson

[57] ABSTRACT

The present invention relates to the use of certain β-adrenergic agonists to reduce a wasting condition in a mammal (e.g., human).

18 Claims, No Drawings

β-ADRENERGIC AGONISTS TO REDUCE A WASTING CONDITION

This application claims priority from provisional application U.S. Ser. No. 60/049,584 filed Jun. 13, 1997.

FIELD OF THE INVENTION

The present invention relates to the use of certain β-adrenergic agonists to reduce a wasting condition in a mammal (e.g., a human).

BACKGROUND OF THE INVENTION

The compounds of the present invention and the pharmaceutically acceptable salts thereof were described in commonly assigned PCT publication WO 96/35671 (published Nov. 14, 1996 from PCT application Number PCT/IB95/00344 filed May 10, 1995) and PCT publication WO 96/35670 (published Nov. 14, 1996 from PCT application Number PCT/IB95/00342 filed May 10, 1995) the disclosures of which are hereby incorporated by reference. In those publications the compounds were described for the treatment of hyperglycemia and obesity.

β-Adrenergic receptors have been categorized into $\beta_1$, $\beta_2$ and $\beta_3$-subtypes. Agonists of β-receptors promote the activation of adenyl cyclase. Activation of $\beta_1$-receptors invokes increases in heart rate while activation of $\beta_2$-receptors induces relaxation of skeletal muscle tissue which produces a drop in blood pressure and the onset of smooth muscle tremors. Activation of $\beta_3$-receptors is known to stimulate lipolysis (the breakdown of adipose tissue triglycerides to glycerol and free fatty acids) and metabolic rate (energy expenditure), and thereby promote the loss of fat mass. Compounds that stimulate β-receptors are therefore useful as anti-obesity agents, and can also be used to increase the content of lean meat in edible animals. In addition, compounds which are $\beta_3$-receptor agonists have hypoglycemic or anti-diabetic activity, but the mechanism of this effect is unknown.

Until recently $\beta_3$-adrenergic receptors were thought to be found predominantly in adipose tissue. $\beta_3$-receptors are now known to be located in such diverse tissues as the intestine (*J. Clin. Invest.*, 91, 344 (1993)) and the brain (*Eur. J. Pharm.*, 219,193 (1992)). Stimulation of the $\beta_3$-receptor has been demonstrated to cause relaxation of smooth muscle in colon, trachea and bronchi. *Life Sciences*, 44(19), 1411 (1989); *Br. J. Pharm.*, 112, 55 (1994); *Br. J. Pharmacol.*, 110, 1311 (1993). For example, stimulation of $\beta_3$-receptors has been found to induce relaxation of histamine-contracted guinea pig ileum, *J.Pharm.Exp.Ther.*, 260, 1, 192 (1992).

U.S. Pat. No. 5,597,843 discloses the use of a substituted 1, 3-benzodioxole to reduce a wasting condition. Various physiologic pathologies and metabolic states in a subject can produce a wasting condition that is characterized, in part, by a progressive loss of body, organ or tissue mass. A wasting condition can occur as a result of a pathology such as cancer or can be due to a physiologic or metabolic state such as the disuse deconditioning that can occur, for example, due to prolonged bed rest or due to the weightlessness associated with space flight or age associated muscle mass and strength decline.

In most cases, minimal loss of body mass is of little concern. For example, a minimal loss of body mass can occur in a subject having a brief illness but an otherwise normal nutritional status. In this case, the lost body mass is quickly regained after the illness runs its course. Loss of body mass can become critical, however, during a prolonged illness, where nutritional depletion can occur, or when a weight bearing load is removed from the musculo-skeletal system for an extended period of time. Removal of a weight bearing load can occur, for example, due to long term bed rest, immobilization of a limb or simulated or actual weightlessness such as during space flight.

The loss of body mass that occurs during a wasting condition can be characterized by a loss of total body weight, a loss of organ weight such as a loss of bone or muscle mass or to a decrease in tissue protein. In addition, the loss of body mass associated with a wasting condition can be localized or systemic. For example, localized loss of body mass can occur due to denervation of a muscle or to the disuse deconditioning that occurs when a limb is immobilized in a cast. Systemic loss of body mass can result, for example, due to the disuse deconditioning that occurs during space flight or due to a pathology such as cancer.

A wasting condition, if unabated, can have dire health consequences. For example, the changes that occur during a wasting condition can lead to a weakened physical state that is detrimental to an individual's health. The severe wasting or cachexia associated with cancer, for example, can prolong patient convalescence and decrease the patient's quality of life.

Three general approaches have been utilized to reduce a wasting condition in a subject. One approach has been to alter the systemic stress response that is induced due to acute injury or illness. For example, an attempt has been made to manipulate the signals mediated by cytokines or lipids, which are involved in regulating the stress response.

Another approach to reduce a wasting condition has been to administer supplemental nutrition. In many cases, however, even when a subject is maintained on a program of total parenteral nutrition over several weeks, loss of body mass continues and no increase in muscle mass occurs. Thus, simple replacement of any deficient caloric intake is insufficient, alone, to alleviate an undesirable loss of body mass.

Nutritional supplementation has been used in combination with the administration of anabolic agents in an attempt to reduce wasting. This combined approach currently is the preferred method of treatment and can effectively counteract the loss of body mass that occurs due to acute illness, disuse deconditioning and cachexia.

Various anabolic agents, including anabolic steroids, growth hormone, insulin-like growth factors and beta adrenergic agonists, have been used in the combined modality protocol. Unfortunately, the usefulness of anabolic agents is limited by undesirable side effects. For example, anabolic steroids can cause adverse effects in the liver and in the cardiovascular and reproductive systems of a treated individual and can affect the psychological status of the subject. Other anabolic agents such as growth hormone and insulin-like growth factors can induce diabetes, hypothyroidism and arthritis as well as acromegaly, which is associated with myopathy, peripheral neuropathy and cardiac disease.

The β2 adrenergic agonists clenbuterol and salbutamol are anabolic agents that can reduce weight loss, particularly loss of muscle mass and bone density (see Kim and Sainz, *Life Sci.* 50:397–407 (1992)). However, β2 agonists can produce undesirable side effects, including increased heart rate, decreased blood pressure or muscle tremor, in a treated subject. These agents also can produce undesirable behavioral changes.

Thus, a need exists to identify pharmaceutical agents that effectively reduce a wasting condition in a subject without producing significant adverse side effects.

SUMMARY OF THE INVENTION

The present invention provides methods of using certain β-agonists to reduce loss of body mass that occurs in a wasting condition.

The present invention provides a method for reducing a wasting condition in a mammal (e.g., human) by administering a Formula I compound or salt or prodrug thereof to reduce the loss of body mass associated with a wasting condition caused by a pathologic, physiologic or metabolic state in a subject. The invention provides methods for reducing a wasting condition due, for example, to cancer, disuse deconditioning, denervation of a muscle or an acute inflammatory response in a mammal.

The Formula I compounds have the formula.

FORMULA I

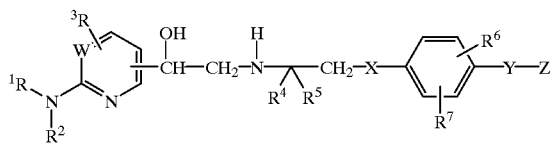

wherein:

$R^1$, $R^2$, $R^4$ and $R^5$ are independently hydrogen or $(C_1-C_6)$ alkyl;

$R^3$, $R^6$ and $R^7$ are independently hydrogen, halogen, $(C_1-C_6)$alkyl, nitro, cyano, trifluoromethyl, $SO_2R^8$, $SO_2NR^9R^{10}$, $NR^9R^{10}$, $COR^{11}$, $CO^2R^9$, $(C_1-C_6)$alkoxy, $NR^9SO_2R^8$, $NR^9COR^{11}$, $NR^9CO_2R^9$ or $OR^9$;

$R^8$ is independently $(C_1-C_6)$alkyl or $(C_1-C_6)$alkoxy $(C_1-C_6)$alkyl;

$R^9$ and $R^{10}$ are independently hydrogen, $(C_1-C_6)$alkyl, $(C_3-C_8)$cycloalkyl, or $(C_1-C_6)$alkoxy$(C_1-C_6)$alkyl;

$R^{11}$ is independently hydrogen, $(C_1-C_6)$alkyl, $NR^9R^{10}$, $(C_3-C_8)$cycloalkyl, or $(C_1-C_6)$alkoxy$(C_1-C_6)$alkyl wherein $R^9$ and $R^{10}$ are as defined above;

$R^{12}$ is independently H or $(C_1-C_6)$ alkyl;

W is N, CH, or when $R^3$ is bonded to W, $CR^3$ wherein $R^3$ can be any of the values listed above for $R^3$ in addition to H;

X and Y are independently a direct link (i.e., a covalent bond), oxygen, sulfur, or $NR^1$ wherein $R^1$ is as defined above;

Z is $(CH_2)_nCO_2R^{12}$, $(CH_2)_n$—O—$(CH_2)_mCO_2R^{12}$, $(CH_2)_m$ $OR^9$, $(CH_2)_nCOR^{11}$, $(CH_2)_nSO_2NR^9R^{10}$, $(CH_2)_n$—$NR^9SO_2R^8$, $(CH_2)_nP(O)(OR^1)(OR^2)$, $(CH_2)_n$—O—$(CH_2)_mCOR^{11}$, $(CH_2)_n$—O—$(CH_2)_mP(O)(OR^1)(OR^2)$, $(CH_2)_n$—O—$(CH_2)_mSO_2NR^9R^{10}$, or $(CH_2)_n$—O—$(CH_2)_m$—$NR^9SO_2R^8$;

m is 1 to 6;

n is 0 to 6, provided that if Y is O or S, n is not 0;

or, pharmaceutically acceptable prodrugs of said compounds; or pharmaceutically acceptable salts of said compounds and said prodrugs.

In general, those compounds wherein the Y-Z moiety terminates in a free carboxylic acid (COOH) group constitute a preferred subgroup. This particular group is referred to as "free carboxylic acids" below.

Another preferred subgroup of compounds includes those free carboxylic acids of formula I wherein X is oxygen.

Another preferred subgroup includes those free carboxylic acids of formula I wherein X is oxygen and W is CH.

Another preferred subgroup includes those free carboxylic acids of formula I wherein X is oxygen, W is CH, and each of $R^1$, $R^2$, $R^3$, $R^4$, $R^5$, $R^6$, and $R^7$ is H.

Another preferred subgroup includes those compounds of formula I wherein X is oxygen, W is CH, each of $R^1$, $R^2$, $R^3$, $R^4$, $R^5$, $R^6$, and $R^7$ is H, and Y is oxygen or a direct link.

Specific compounds include the following:

(4-(2-(2-(6-aminopyridin-3-yl)-2(R)-hydroxyethylamino) ethoxy)phenyl)acetic acid;

(4-(2-(2-(6-aminopyridin-3-yl)-2(R)-hydroxyethylamino) ethoxy)phenoxy)acetic acid;

4-(2-(2-(6-aminopyridin-3-yl)-2(R)-hydroxyethylamino) ethoxy)benzoic acid; and (4-(2-(2-(6-aminopyridin-3-yl)-2(R)-hydroxyethylamino) ethoxy)phenyl) propionic acid.

The invention also provides methods of administering a pharmaceutical composition comprising a Formula I compound or salt or prodrug thereof to a mammal (e.g., a human) to reduce a wasting condition in the subject. The composition can be administered to a subject to reduce the wasting that can occur due, for example, to an acute inflammatory response, to cachexia, or to prolonged disuse of a muscle or muscle group.

In a preferred aspect of this invention the wasting condition is due to a pathology.

An especially preferred aspect of this invention is wherein the pathology is cancer.

An especially preferred aspect of this invention is wherein the pathology is an acute inflammatory response.

In another preferred aspect of this invention the wasting condition is due to disuse deconditioning.

In another preferred aspect of this invention the wasting condition is an age associated decline in muscle mass strength.

An especially preferred aspect of this invention is wherein the disuse conditioning occurs due to weightlessness.

An especially preferred aspect of this invention is wherein the disuse conditioning occurs due to immobilization.

In yet another preferred aspect of this invention the wasting condition is due to muscle denervation.

In yet another preferred aspect of this invention the wasting condition is muscle wasting.

The term "a wasting condition" is used broadly to mean an abnormal, measurable decrease in body, organ or tissue weight. Such an abnormal decrease, which can be due, for example, to a decrease in muscle or bone mass or tissue protein, can be measured by weighing the subject or by measuring the circumference, for example, of one or more limbs of the subject.

As used herein, the term "reducing" has its commonly understood meaning of lessening or decreasing.

This invention includes prodrugs of compounds of Formula I having free amino, amido, hydroxy or carboxylic groups. Prodrugs are understood to comprise an amino acid residue, or a polypeptide chain of two or more (e.g., two, three or four) amino acid residues which are covalently joined through peptide bonds to free amino, hydroxy or carboxylic acid groups of compounds of Formula I. The amino acid residues include the 20 naturally occurring amino acids commonly designated by three letter symbols and also include, by way of example and not of limitation, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs are also understood to include carbonates, carbamates, amides and alkyl esters which are covalently bonded to the above substituents of Formula I through the carbonyl carbon prodrug sidechain. Prodrugs also include compounds in which the secondary amine and its 13-hydroxy when taken together form a group of the formula

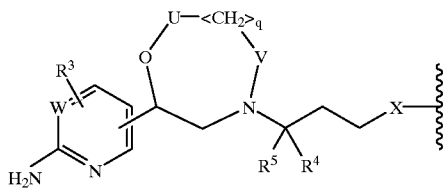

wherein $R^3$, $R^4$, $R^5$ and X are as defined above for Formula I, q is 0 to 6, and U and V are independently carbonyl, methylene, $SO_2$ or $SO_3$, wherein methylene is optionally substituted with hydroxy.

It will be appreciated by those skilled in the art that compounds of Formula I contain at least one chiral center, and possibly two chiral centers when $R^4$ and $R^5$ are different. Accordingly compounds of Formula I may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of the utilities noted herein, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of the said utilities by the standard tests described hereinafter. In general, (R)-stereochemistry is preferred at all chiral centers in the compounds of this invention.

The terms "alkyl" and "alkoxy" as used herein, include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo", as used herein, unless otherwise indicated, includes chloro, fluoro, bromo and iodo.

The term "treating" as used herein includes preventative as well as disease remitative treatment.

Particular values of $(C_1-C_6)$alkyl include methyl, ethyl, propyl, isopropyl, butyl, isobutyl, t-butyl, pentyl, isopentyl, and hexyl.

Particular values of $(C_1-C_6)$alkoxy include methoxy, ethoxy, propoxy, isopropoxy, butoxy, isobutoxy, t-butoxy, pentoxy, isopentoxy, and hexoxy.

Particular values of $(C_3-C_8)$cycloalkyl include cyclopropyl, cyclobutyl, cyclopentyl, cyclohexyl, and cycloheptyl.

More particular values of $(C_1-C_6)$alkyl include the values of $(C_1-C_3)$alkyl, including methyl, ethyl, propyl, and isopropyl.

More particular values of $(C_1-C_6)$alkoxy include the values of $(C_1-C_3)$alkoxy, including methoxy, ethoxy, propoxy, and isopropoxy.

Common chemical acronyms and abbreviations are used herin. These acronyms and abbreviations include BOC, meaning tert-butoxycarbonyl; Cbz, meaning benzyloxycarbonyl; THF, meaning tetrahydrofuran; DMF, meaning dimethylformamide; NMP, meaning N-methyl-2-pyrrolidinone; DMAC, meaning N,N-dimethylacetamide; DME, meaning 1,2-dimethoxyethane; DMSO, meaning dimethylsulfoxide; and TFA, meaning trifluoroacetic acid. As used herein "Lower" means $(C_1-C_3)$ for example, when referring to a lower alkyl group or a lower alkanol.

DETAILED DESCRIPTION

The present invention provides methods for reducing a wasting condition in a subject by administering to the subject the compounds of this invention. To reiterate, the compounds used herein have been described previously in commonly assigned PCT publication WO 96/35671 (published Nov. 14, 1996 from PCT application Number PCT/IB95/00344 filed May 10, 1995) and PCT publication WO 96/35670 (published Nov. 14, 1996 from PCT application Number PCT/IB95/00342 filed May 10, 1995) the disclosures of which are hereby incorporated by reference.

However, to facilitate the practice of this invention a further description of the compounds used herein is provided for below.

Compounds of Formula I can be made by processes which include analogous processes known in the chemical arts for the production of other compounds. Such processes for the manufacture of a compound of Formula I as defined above are provided as further features of the invention and are illustrated by the following procedures in which the meanings of generic radicals are as given above unless otherwise defined. The processes can be effected, generally:

(a) for a compound of Formula I wherein W is CH and $R^1$ and $R^2$ are H, by reducing a compound of formula II

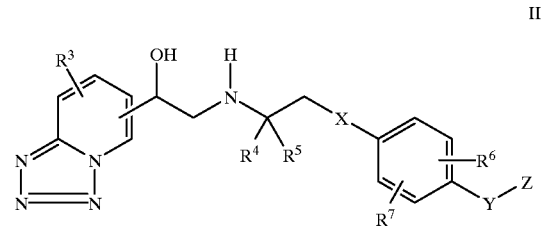

with an appropriate reducing agent. The reaction is conducted employing a reducing agent as known in the art such as stannous chloride, zinc chloride, or hydrogen in the presence of (e.g., 10%) palladium-on-carbon catalyst. The reaction is typically implemented by refluxing in a polar solvent such as a lower alcohol, for example methanol or ethanol.

(b) for a compound of Formula I wherein $R^1$ and $R^2$ are H, by deprotecting a compound of formula III

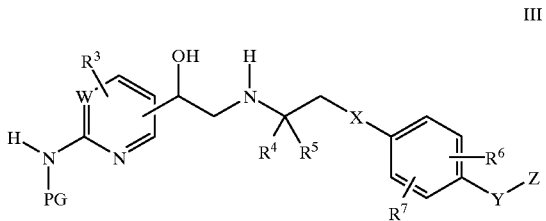

wherein PG is a (conventional) protecting group, preferably a $(C_1-C_6)$acyl (for example, acetyl), a benzyloxycarbonyl (Cbz) or t-butoxycarbonyl (BOC) group, as known in the art. The reaction can be implemented conventionally by hydrogenation, or with a deprotecting reagent such as an acid (e.g., trifluoroacetic acid or a mineral acid such as HCl) in aqueous/alcoholic solvent medium.

(c) for a compound of Formula I wherein Z terminates in a carboxylic acid moiety (i.e., the free acid), by hydrolyzing a compound of Formula I which is a corresponding ($C_1$–$C_6$)alkyl ester to the said free acid. The reaction can be conducted conventionally employing a base such as an alkali metal hydroxide in at least a stoichiometric amount, and preferably in excess (e.g., up to a base:compound molar ratio of 5:1), at reflux in aqueous/lower alcohol solvent medium or with an excess of mineral acid in water.

(d) for a compound of Formula I wherein Z terminates in a mono- or di-substituted amide moiety, by treating a compound of Formula I which is a corresponding ($C_1$–$C_6$)alkyl ester with a corresponding mono- or di-substituted amine. The reaction can be implemented as a one-step displacement conventionally, at reflux in aqueous/lower alcohol solvent medium.

(e) for a compound of Formula I wherein $R^1$ and/or $R^2$ are other than H, by treating a compound of formula XXX

XXX

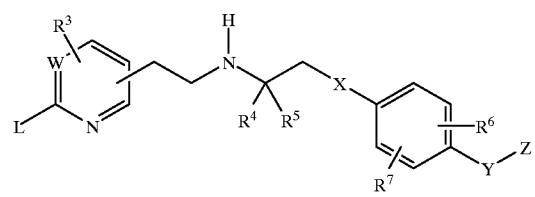

wherein L is a displaceable group, with a corresponding amine of formula $HNR^1R^2$. The reaction is typically conducted in a lower alcohol at reflux.

Methods (c) and (d) are further discussed in Reaction Scheme 5 below.

If they are not commercially available, the necessary starting materials for the above procedures may be made by procedures which are selected from standard organic chemical techniques, techniques which are analogous to the synthesis of known compounds, or techniques which are analogous to the above described procedures or the procedures described in the examples. In particular, the processes and products of the present invention are illustrated in the following reaction schemes wherein, unless otherwise indicated, all variables are as previously defined.

SCHEME 1

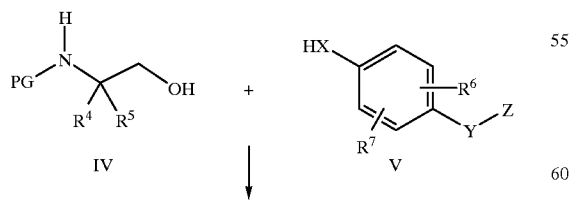

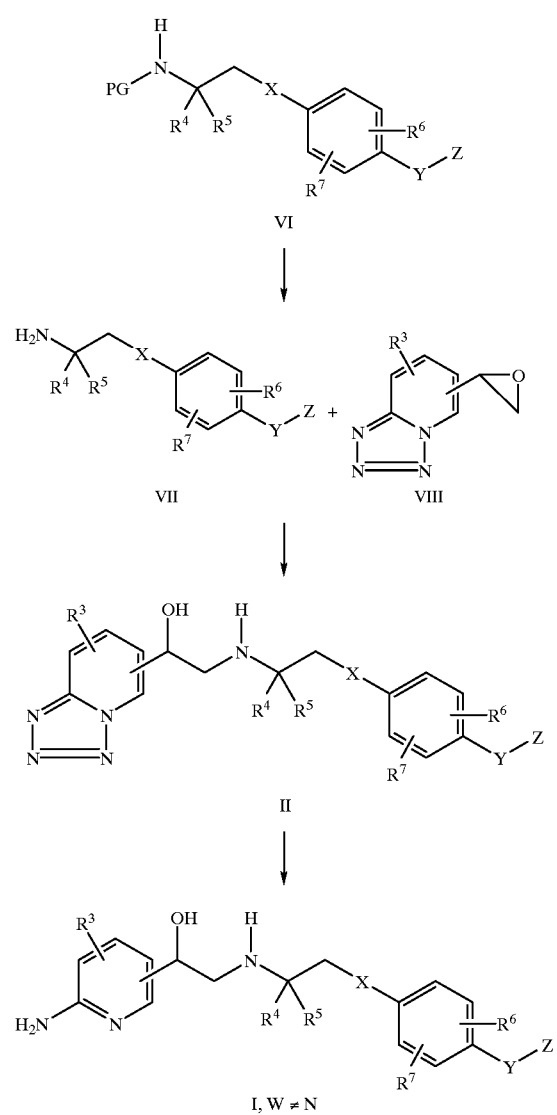

SCHEME 2

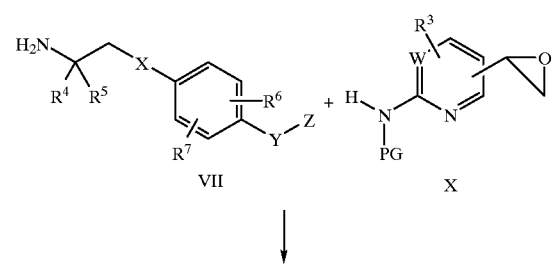

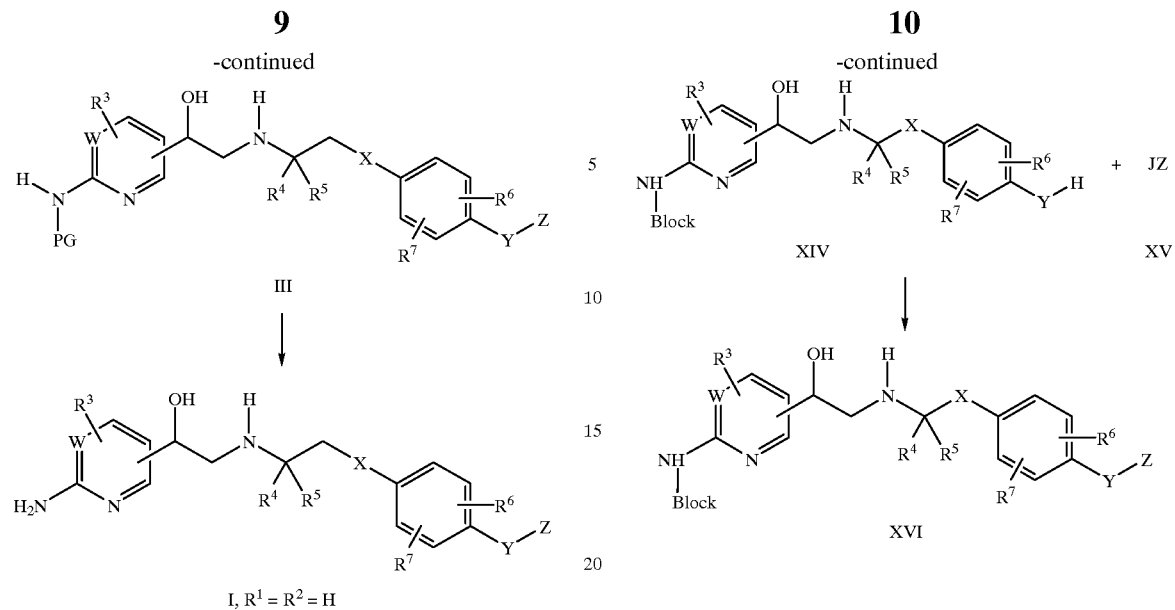
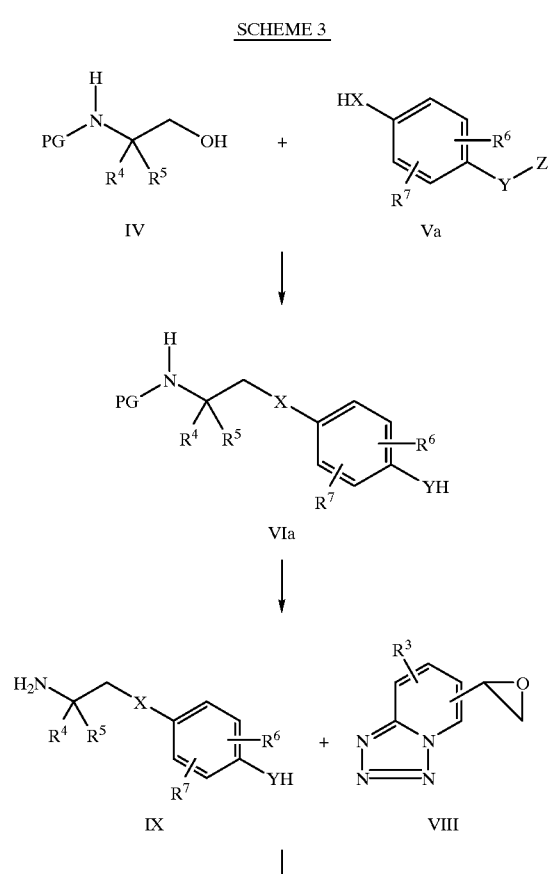
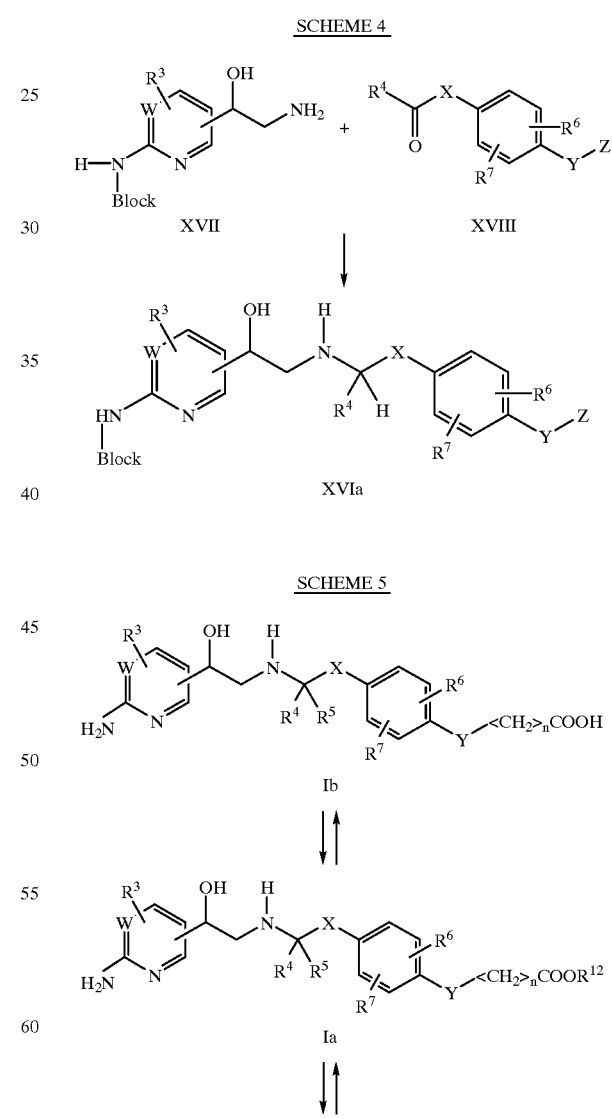

11
-continued
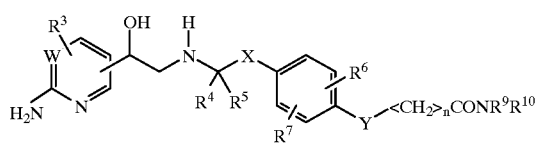
SCHEME 6
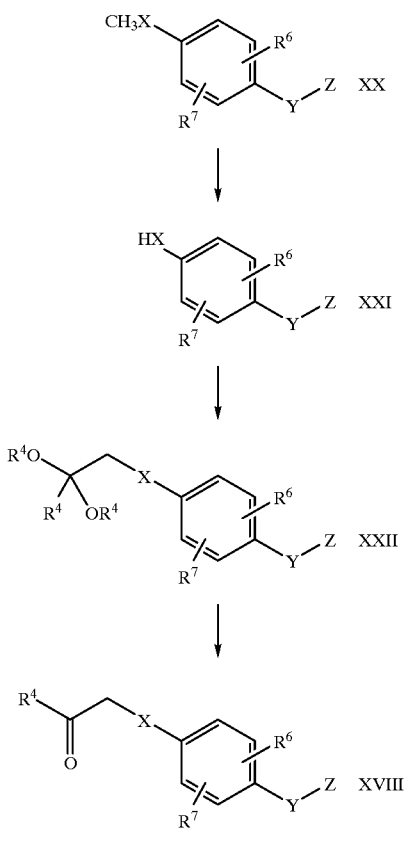
SCHEME 7
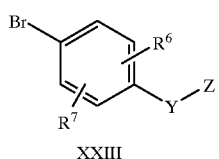
12
-continued
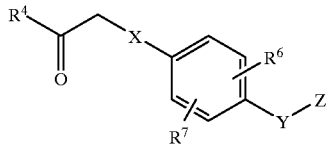
XVIII
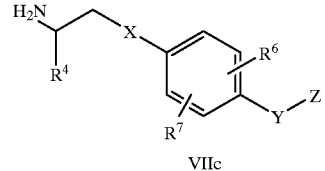
VIIc
SCHEME 8
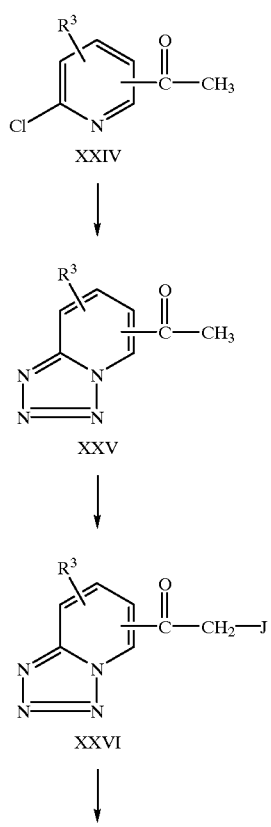
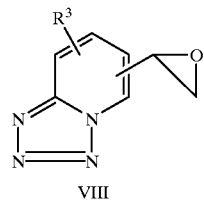

SCHEME 9

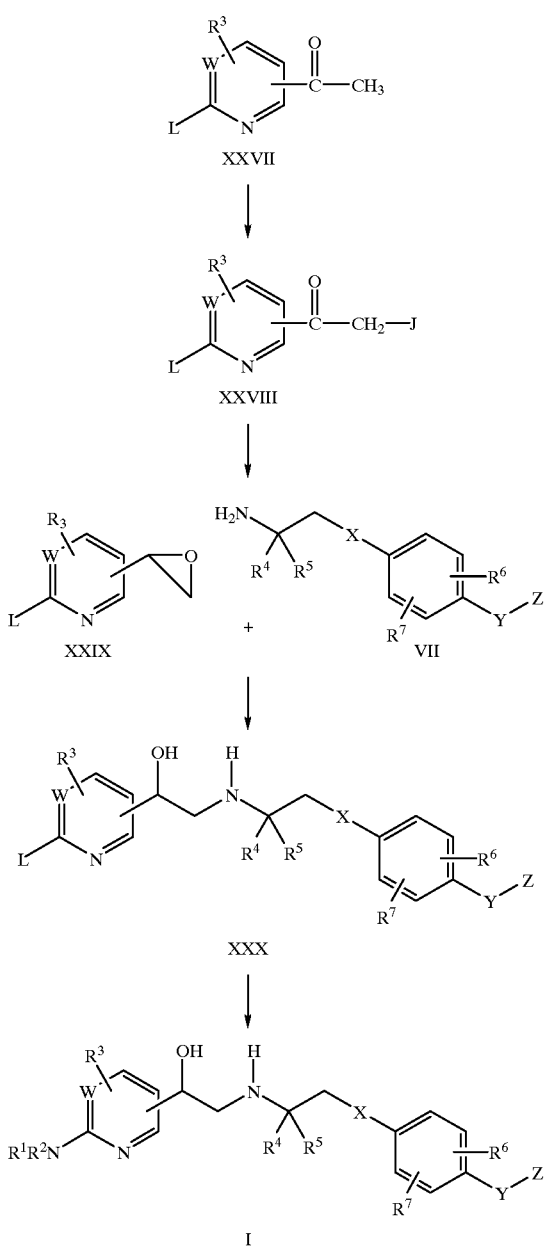

In the discussion which follows, common chemical acronyms and abbreviations have been used: BOC (tert-butoxycarbonyl); Cbz (benzyloxycarbonyl); THF (tetrahydrofuran); DMF (dimethylformamide); DMSO (dimethylsulfoxide); TFA (trifluoroacetic acid). "Lower" as used herein (for example, when referring to a lower alkyl group or a lower alkanol) means ($C_1$–$C_3$).

Preparation of a tetrazole of formula II (and its conversion to a compound of Formula I) is illustrated in Scheme I. Amino alcohol IV, wherein PG is a standard protecting group such as BOC, Cbz, or an ($C_1$–$C_6$)alkylcarbonyl group, is first dehydratively coupled with compound V in a so-called Mitsunobo reaction to make (protected) product amine VI. The reaction is typically conducted with stirring and at room temperature (or higher if preferred) in the presence of a dehydrating agent such as a stoichiometric quantity of diethylazodicarboxylate and a phosphine, for example triphenylphosphine. The reaction can be implemented in any inert solvent such as THF, benzene, toluene, halogenated hydrocarbons, DMF, or DMSO.

Protected amine VI can then be deprotected as known in the art to yield amine VII, for example with an inorganic acid or organic acid such as TFA in an inert solvent such as a halogenated hydrocarbon (e.g., chloroform or methylene dichloride), at room temperature for a reaction time typically of about 2 to about 8 hours. Alternatively, the protecting group PG can be removed by hydrogenolysis using hydrogen in the presence of a palladium-on-carbon catalyst and in an inert solvent such as a lower alcohol or DMF. The hydrogenolysis is typically implemented anywhere from room temperature up to about 90° C.

The amine of formula VII can then be treated with an azo-protected epoxide of formula VII to yield compound 11. This reaction is typically carried out by reacting the amine of formula VII and the epoxide of formula VII in a polar aprotic solvent such as dimethyl sulfoxide, dimethyl formamide, acetonitrile or a lower alkanol such as ethanol, isopropanol or butanol, at a temperature from about –10° C. to about 125° C.

A preferred modification of the above reaction involves pretreatment of the amine of formula VII with an N-(trialkylsilyl)acetamide, for example N-(trimethylsilyl)acetamide, to form a silylated compound of the formula VIIa

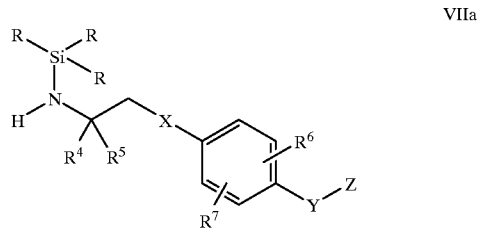

wherein R is typically a lower alkyl group. This reaction is typically carried out in a polar aprotic solvent such as DMSO, DMF, or acetonitrile, at a temperature from about –10° C. to about 125° C. Preferably, the silylation is carried out at about 25° C. and the reaction with the epoxide is accomplished at about 60° C. After silylation is complete, the compound of formula VIIa is reacted with the epoxide of formula VIII, as described above to form the intermediate of formula IIa.

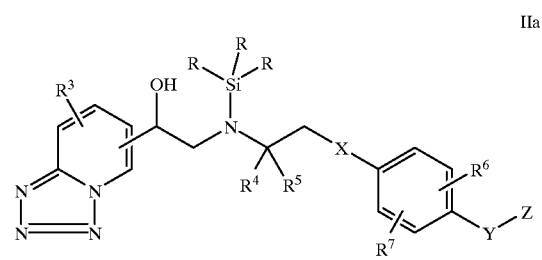

After the reaction is complete or has otherwise been terminated, the silyl group can be removed by standard means such as by mild acid or base hydrolysis.

It is noted that a silylated derivative of the formula

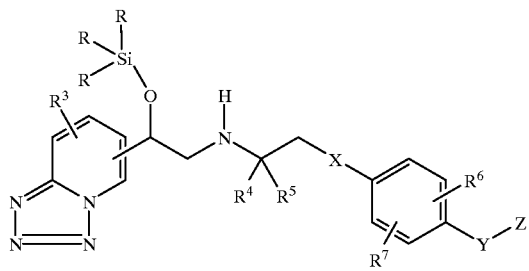

will also be produced, in many cases as the major isomer. The above isomer can also be deprotected by the same standard means.

Following removal of the trialkylsilyl protecting group, compound 11 can be reduced to convert the tetrazole portion of the molecule to the corresponding pyridyl amine by treatment with a suitable reducing agent, as described above in (a).

Scheme 2 illustrates the preparation of a compound of formula I using a precursor compound of formula II. An epoxide of formula X, wherein W and protecting group PG are as previously defined, can be reacted with amine VII under standard conditions, for example using a polar solvent such as a lower alcohol and implementing the reaction at reflux, typically for a time between 2 and 8 hours. In a preferred embodiment, amine VII is first silylated as described above to make a silylated amine compound of formula VIIa above prior to treating it with epoxide X.

Scheme 3 illustrates the preparation of a compound of formula XVI which is generic to both intermediates of formulae II and III when Y is O, S, or NH. Amino alcohol IV may first be reacted with compound Va, as described for the reaction of amino alcohol IV with compound V for Scheme 1. If X and Y are the same, then the YH moiety need not be protected by pre-reacting with a blocking reagent. If X and Y are different, however, then protecting the YH moiety by standard means, for example by pre-reacting it with an aromatic or aliphatic carboxylic acid, is preferred. De-protection by standard means (e.g. alkaline hydrolysis) can then be effected at essentially any point prior to reacting with compound XV (JZ), described below. The product, compound VIa, can then be de-protected as described for compound VI, Scheme 1, thereby yielding compound IX. Compound IX can be reacted with azo-protected epoxide VIII, as described for the reaction of compounds VII and VIII, Scheme 1. Compound XVI may then be made by reacting compounds XIV and XV, wherein J is a leaving group such as chloro, bromo, or iodo. It is understood that for compound XIV, when W is CH, the "block" moiety attached to the amino group is in the form of a protecting azo group completing a fused tetrazole moiety and compound XVI is then the same as compound II. Or, when W is CH or N, the "block" moiety can additionally be any conventional protecting group, defined hereinbefore as "PG", and structure XVI is then the same as compound III. In either case compounds XIV and XV can be reacted in an inert aprotic solvent such as DMF, DMSO, or toluene and in the presence of a base such as an alkali metal hydride or carbonate (for example sodium hydride or potassium carbonate). The reaction is allowed to proceed typically at ambient temperature and for a period of 1 to 8 hours.

Scheme 4 illustrates the preparation, via reductive amination, of compound XVIa, a subset of formula XVI wherein at least one of $R^4$ and $R^5$ is H and the other of $R^4$ and $R^5$ is H or $(C_1-C_6)$alkyl. Amine XVII and ketone (or aldehyde if $R^4$ is H) XVIII are reacted to produce a compound of formula XVIa. This reaction is typically carried out in the presence of a reducing agent such as sodium cyanoborohydride, sodium triacetoxyborohydride, sodium borohydride, hydrogen and a metal catalyst, zinc and hydrochloric acid, or borane dimethyl sulfide followed by treatment with formic acid. It is generally conducted at temperatures from about −60° C. to about 50° C. Suitable reaction inert solvents for this reaction include lower alcohols (e.g., methanol, ethanol and isopropanol), acetic acid, chlorinated hydrocarbon solvents (e.g., methylene chloride, chloroform, 1,2 dichloroethane) and THF. Preferably, the solvent is 1,2-dichloroethane, the temperature is about 25° C., and the reducing agent is sodium triacetoxyborohydride.

Scheme 5 illustrates the preparation of free acids and amides of formula Ib and Ic from compounds of formula Ia, as set forth in (c) and (d) above. The use of formula Ia, Ib, and Ic in Scheme 5 is exemplary. Compounds of formula Ib and Ic are, respectively, compounds of Formula I in which Z is $(CH_2)_nCO_2H$ and $(CH_2)_nCOR^{11}$ wherein $R^{11}$ is $NR^9R^{10}$. Scheme 5 applies equally to compounds analogous to formula Ib in which Z is $(CH_2)_n$—O—$(CH_2)_mCO_2H$, and to compounds analogous to formula Ic in which Z is $(CH_2)_n$—O—$(CH_2)_mCOR^{11}$ where $R^{11}$ is $NR^9R^{10}$, and $R^9$, $R^{10}$, n and m are as previously defined. Compounds of formula Ia are intermediates corresponding to formula I except that the value corresponding to Z is $(CH_2)_nCO_2R^{12}$ wherein $R_{12}$ is an alkyl group, typically $(C_1-C_6)$alkyl, although other replaceable groups such as $(C_3-C_8)$ cycloalkyl can also be employed. Intermediates corresponding to formula Ia except that the value corresponding to Z is $(CH_2)_n$—O—$(CH_2)_mCO_2R^{12}$ are also useful for making compounds according to the invention. Intermediate compounds of formula Ia are prepared by the methods of Schemes 1, 2, and 3. The transformations depicted in Scheme 5 may be accomplished by methods well known to those skilled in the art. It is noted that the reaction conditions can be adapted so the reverse reactions are favored, though implementation of such conditions is less likely since the free acids are preferred.

Referring to Scheme 5, compounds of formula Ia can be converted into carboxylic acids of formula Ib by treatment with an acid or a base. Examples of suitable bases for the reaction are: sodium hydroxide (NaOH), potassium hydroxide (KOH), and lithium hydroxide. Suitable acids for the reaction include: hydrochloric acid (HCl), hydrobromic acid and sulfuric acid. Preferably, the base is potassium hydroxide. The solvent for the aforesaid process is typically a lower alkanol, hexane, DMF, toluene and/or water. The lower alkanol can be methanol, ethanol, propanol or butanol. The reaction temperature may range from about 0° C. to about 100° C. Preferably, the temperature is about 25° C.

Alternatively, compounds of formula Ia can be converted into amides of formula Ic by treatment of an ester of formula Ia with an amine of the formula $R^9R^{10}NH$. Usually, a polar protic solvent such as a lower alkanol is used, and the reaction is run at a temperature from about 0° C. to about 125° C. for about 0.5 to about 24 hours. Suitable solvents include lower alcohols, and mixtures thereof with toluene, cyclohexane, DMF and methylene chloride. Preferably, the reaction is conducted in methanol at about 65° C. for about 3 to about 24 hours.

Scheme 6 refers to the preparation of compounds of formula VII wherein at least one of $R^4$ and $R^5$ is H, and XVIII wherein X is O or S. Compounds of formula VII wherein at least one of $R^4$ and $R^5$ is H are labeled as VIIc in Scheme 6. For exemplification only, $R^4$ is illustrated as the variable which can assume values other than H, although it is to be understood that $R^5$ can be the variable as well. Compounds of formula VIIc and XVIII are starting materials for the synthesis, respectively, of intermediates of formula II and III in Schemes 1 and 2, and of formula XVIa in Scheme 4, which intermediates can in turn be used to make compounds of Formula I.

Referring to Scheme 6, compounds of formula VIIc are made by reductive amination of a compound of formula XVIII. The conditions for reductive amination are as described above for the conversion of a ketone (or aldehyde, as appropriate) of formula XVIII to a compound of formula XVIa in Scheme 4, with the exception that the amine used is ammonia or an acid addition salt thereof, instead of the amine of formula XVII.

Compounds of formula XVIII can be made in three steps beginning with compounds of the formula XX.

Compounds of the formula XX are first converted to thiols or phenols of the formula XXI by treatment of an ether (when X is O) or a thioether (when X is S) of formula XX with boron tribromide. Suitable solvents for the aforesaid reaction are non-polar aprotic solvents such as methylene chloride, toluene, chloroform, or carbon tetrachloride. Preferably, the solvent is methylene chloride. The temperature of the reaction may range from about −78° C. to about 20° C. during the reaction with boron tribromide. It is preferably about 0° C.

The thiol or phenol of formula XXI so formed is converted into a ketal or acetal of the formula XXII by treatment with a compound of the formula

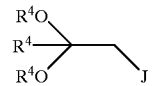

wherein J is chloro, bromo or iodo, in the presence of a base. Preferably, the thiol or phenol of formula XXI is first converted into an anion by reaction with a base. Examples of appropriate bases include sodium hydride and potassium t-butoxide. The preferred base is sodium hydride (NaH). Examples of suitable solvents for the aforesaid process include polar aprotic solvents such as dimethyl formamide, dimethylsulfoxide, and sulfolane. Preferably, the solvent is dimethyl formamide.

The temperature for the aforesaid reaction is in the range of about −10° C. to about 100° C. Preferably, the temperature is 30° C.

The ketal or acetal of formula XXII so formed is converted into the corresponding compound of formula XVIII by reaction with an acid. Typically, this reaction is conducted at a temperature in the range of about 10° C. to about 100° C. Examples of appropriate acids for the aforesaid process are hydrochloric, hydrobromic and sulfuric acids. Preferably, the acid is hydrochloric acid. Suitable solvents for the aforesaid process include polar solvents such as acetone and/or water. Preferably, the solvent is acetone.

Scheme 7 refers to the preparation of compounds of the formula VIIc and XVIII wherein X is a direct link and at least one of $R^4$ and $R^5$ is H, with the remaining member of $R^4$ and $R^5$ being H or $(C_1-C_6)$alkyl. Again, the single variable value $R^4$ is shown for purposes of illustration. Compounds of the formula VIIc and XVIII are starting materials for the synthesis of corresponding intermediates useful in the invention as illustrated in Schemes 1, 2 and 4.

Compounds of formula XVIII, wherein X is a direct link, can be used to form intermediates of formula XVIa according to the processes of Scheme 4.

Compounds of the formula VIIc, wherein X is a direct link, can be used to form corresponding compounds of Formula I according to the processes of Schemes 1 and 2.

Referring to Scheme 7 (wherein X is a direct link), a compound of formula XVIII can be converted into a compound of formula VIIc by reductive amination of a compound of the formula XVIII with ammonia as described above for Scheme 6.

A compound of formula XVIII can be prepared from a corresponding compound of formula XXIII, by treatment of a compound of the formula XXIII with a tin reagent of the formula $R^4COCH_2Sn(CH_3CH_2CH_2CH_3)_3$ in the presence of palladium (II) acetate and tri-o-tolylphosphine. The tin reagent, $R^4COCH_2Sn(CH_3CH_2CH_2CH_3)_3$, is formed by reaction of tributyltin methoxide with a compound of the formula

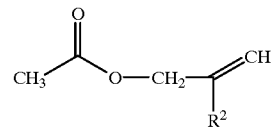

Suitable solvents for the aforesaid process include non-polar solvents such as toluene, benzene and hexane. Preferably, the solvent is toluene. The temperature for the aforesaid process is generally in the range of about 10° C. to about 150° C., and is preferably about 95° C.

Scheme 8 illustrates the preparation of an epoxide of formula VIII, which is used to make an intermediate of formula II and, in turn, a compound of Formula I wherein W is CH. The preparation is generally according to methods disclosed in U.S. Pat. Nos. 4,358,455 and 5,019,578. A ketone of formula XXIV can be treated with sodium azide in the presence of an acid such as any of the common mineral acids (e.g., HCl) at reflux in a protic solvent such as aqueous alcohol to yield a tetrazole of formula XXV. Tetrazole XXV can then be treated, preferably with a halogenating agent such as bromine, to yield a corresponding compound of formula XXVI wherein J is a leaving group such as a bromo group. Bromination can be carried out under standard conditions, for example in glacial acetic acid solvent which has been saturated with HBr. Generally the reaction is conducted under chilled (e.g, ice bath) conditions. The compound of formula XXVI can then be converted to the corresponding oxirane VII under standard conditions, for example by treating compound XXVI with a mild reducing agent (e.g., sodium borohydride, lithium borohydride) at room temperature in an inert solvent such as THF, followed by treatment with a base such as an alkali metal hydroxide in a protic solvent such as an alcohol. A stereospecific reducing agent, such as (R)-alpine borane, may be used to prepare the R-isomer of the oxirane, substantially free of the S-isomer.

Scheme 9 illustrates the synthesis of compounds of Formula I when $R^1$ and/or $R^2$ are other than H. A ketone of formula XXVII, wherein L is a group such as F or Cl which can be displaced by a primary or secondary amine, is first treated with a halogenating agent such as bromine to yield a corresponding compound of formula XXVIII wherein J is a leaving group such as a bromo group. Bromination can be effected under standard conditions, for example as described in Scheme 8 for the conversion of tetrazole XXV to compound XXVI. The compound of formula XXVIII can then be converted to the corresponding oxirane XXIX, by the standard procedure also described in Scheme 8. Oxirane XXIX can then be reacted directly with a compound of formula VII, in a polar solvent such as DMSO, DMF, or acetonitrile, at a temperature typically in the range of −10° C. to 125° C., thereby yielding a compound of formula XXX. The intermediate of formula XXX can be reacted in a lower alcohol, at reflux (or under pressure, for example if the amine is gaseous), with an amine of formula $HNR^1R^2$ to produce a corresponding compound of Formula I.

If not commercially available, the necessary starting materials for the chemical reactions disclosed herein may be prepared by procedures which may be selected from standard organic chemical techniques found in standard organic textbook references. The techniques found therein may be applied directly to the synthesis of known starting materials described directly in that reference or may be applied by analogy to compounds having similar functionality to achieve predictable results.

Conventional methods and/or techniques of purification and separation known to those skilled in the art can be used to isolate the compounds of this invention. Such techniques include all types of chromatography (HPLC, column chromatography using common adsorbents such as silica gel, and thin layer chromatography), recrystallization, and differential (i.e., liquid-liquid) extraction techniques.

Certain of the compounds of Formula I, for example those which have free carboxylic acid functionality, form pharmaceutically-acceptable cation salts by reacting the free acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The amino acid prodrugs of this invention may be prepared by conventional peptide coupling reactions coupling a free amino or carboxylic group of the compound of Formula I with an amino acid or a polypeptide, e.g., dipeptide, chain. The coupling reaction is generally conducted at a temperature of about −30° to about 80° C., preferably about 0° to about 25° C. Suitable coupling reagents are usually present, such as dicyclohexylcarbodiimide with hydroxybenzotriazole (HBT), N-3-dimethylaminopropyl-N'-ethylcarbodiimide with HBT, 2-ethoxy-1-ethoxycarbonyl-1,2-dihydroquinoline, carbonyl diimidazole with HBT, or diethylphosphoryl-cyanide. The reaction is generaly conducted in an inert solvent such as acetonitrile, methylene chloride, chloroform, dimethylformamide, dioxane, tetrahydrofuran, dimethoxyethane, or water, or a mixture of two or more such solvents.

Ester, carbonate or carbamate prodrugs of this invention may be prepared by reaction of a free hydroxyl or amino group of the compound of formula I with an activated carbonyl containing molecule such as acetyl chloride or ethyl chloroformate. The reaction can be carried out neat or in the presence of a reaction inert solvent such as methylene chloride, at a temperature from about −78° to about 100° C. Alcohols can also be reacted with cyanogen chloride in the presence of a Lewis acid to form carbamates.

Prodrugs in which the secondary amine and its β-hydroxy, taken together, form a group of the formula

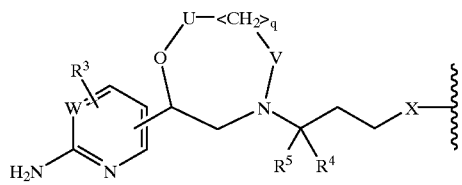

are formed by methods analogous to those described in U.S. Pat. No. 4,593,023, European Patent Application publication no. 170,135A published on Jul. 21, 1984 and U.S. Pat. No. 4,607,033.

Selectivity of a compound for $\beta_3$-receptors over $\beta_2$ and $\beta_1$ receptors may be determined using the following procedures.

In vitro selectivity may be determined by measurement of cyclic adenosine mono-phosphate (cAMP) accumulation in Chinese hamster ovary cells. Chinese hamster ovary cells uniquely transfected with the gene for the human $\beta_1$, $\beta_2$ or $\beta_3$ receptor are grown to confluence in Ham's F12 media containing 10% fetal bovine serum, 500 μg/ml Geneticin, 100 μ/ml penicillin, 100 U/ml streptomycin and 250 ng/ml fungizone. Compounds are prepared as 10mM stock solutions in DMSO (0.1% DMSO, final concentration), diluted in Ham's F12 media and added to the cells at $10^{-10}$–$10^{-5}$ M along with $10^{-3}$ M isobutylmethylxanthine to inhibit phosphodiesterase activity. The media and cells are then incubated for 5 minutes at 37° C. At the end of this period, the media is aspirated and the cells lysed in 0.01 N HCl. The cellular content of cAMP can then be determined by radioimmunoassay (RIA) using a kit from New England Nuclear. There is a direct correlation between the cellular content of cAMP and the agonism of the $\beta_1$, $\beta_2$, or $\beta_3$ receptor. The non-selective adrenergic agonist, norepinephrine, is included as a positive control at $10^{-5}$M. Data are expressed as fold increase over basal.

In vivo selectivity for $\beta_1$ and $\beta_2$ adrenergic receptors may be determined by measurements of heart rate, blood pressure and plasma potassium concentration gathered on conscious catheterized rats (male, Sprague Dawley, 300–380 g body weight). To implant catheters rats are anesthetized with pentobarbital (50–60 mg/kg, i.p.) and the left carotid artery is cannulated with PE50 tubing. The catheter is tunneled subcutaneously, exteriorized at the back of the neck, filled with a solution of polyvinylpyrrolidone in heparinized saline, flame-sealed and taped. Experiments are performed 7 days after surgery. On the day of the experiment, the catheters are untaped and flushed with saline. After at least 30 minutes, basal values for heart rate and blood pressure are measured by attaching the catheter to a pressure transducer, the results recorded on a Grass Model 7 polygraph, and a basal blood sample (0.5 ml) is obtained from the arterial catheter. After obtaining basal values, the test compound or vehicle is administered by oral gavage, and blood pressure (measure of $\beta_2$ activity) and heart rate (measure of $\beta_1$ activity) measurements are taken at 15, 30, 45 and 60 minutes and blood samples for potassium determination ($\beta_2$) are obtained at 30 and 60 min. Isoproternol, a non-selective β-agonist can be tested as a positive control at doses ranging from 0.001 to 1 mg/kg (injected s.c. in saline vehicle). Plasma potassium is determined by flame spectrophotometry. To determine changes, basal values are subtracted from the average of the post dosing values.

The compounds used herein when administered to a subject experiencing a wasting condition, can reduce the rate or amount of body weight loss as compared to the rate or amount of body weight loss that occurs in a subject not receiving the agent.

The abnormal, measurable decrease in body, organ or tissue weight associated with a wasting condition can occur due to various physiologic pathologies and metabolic states, which are generally characterized in being variant from the physiologic and metabolic state of a normal, healthy individual. Thus, the term "wasting condition" refers, for example, to the unwanted decrease in muscle mass that occurs due to prolonged bed rest or immobilization of a limb in a cast or due to denervation of a muscle, to the unhealthy decrease in body weight that can occur during an acute inflammatory response or that occurs in a cancer patient as a result of cachexia or of radiotherapy or chemotherapy, or to the undesirable decrease in body mass due to simulated or actual weightlessness such as occurs during space travel.

The activity of the compounds for the indication claimed herein may be determined by the reduction of the undesirable loss of body weight that occurs due to hindlimb suspension of rats, which is a model for disuse deconditioning (see below).

When treating any of the conditions, disorders and/or diseases previously disclosed herein, generally satisfactory results are obtained when the compounds of the Formula (I), prodrugs, or pharmaceutically acceptable salts thereof are administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally.

By either route, the dosage is in the range of about 0.01 to about 100 mg/kg body weight of the subject per day, preferably about 0.1 to about 50 mg/kg body weight per day, administered singly or as a divided dose. However, the optimum dosage for the individual subject being treated will be determined by the person responsible for the treatment, generally smaller doses being administered initially and thereafter increments made to determine the most suitable dosage. This will vary according to the particular compound employed and with the subject being treated.

Further, although wasting can be localized or systemic (the wasting can be localized as occurs, for example, when a limb is immobilized in a cast, or can be systemic as occurs, for example, due to the cachexia associated with cancer or during prolonged bed rest or weightlessness) the compounds disclosed herein generally are administered such that the agent is distributed systemically in the subject.

The compounds of the present invention are used in combination with a pharmaceutically acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. For parenteral administration the compounds can be combined with sterile aqueous or organic media to form injectable solutions or suspensions. Solutions or suspensions of these active compounds can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly, with intramuscular administration being the preferred parenteral route in man.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The effective dosage of the active ingredient employed may vary depending on the particular compound employed, the mode of administration, the condition being treated and the severity of the condition being treated.

EXAMPLE A

Reduction of Loss of Body Weight Due to Disuse Deconditioning

Disuse deconditioning is effected using the rat hindlimb suspension model, which was developed by the National Aeronautics and Space Administration as a ground based animal model for weightlessness (Morey, *Bioscience* 29:168–172 (1979), which is incorporated herein by reference). This model system involves the use of an x-y axis support system that allows a suspended rat to move freely about its cage. The tail suspension methodology utilizes adhesive foam padded traction tape (Fas-trac) and bias cut stockette. This combination, which results in unloading of the hindlimbs, allows the rat's weight support to be distributed and does not inhibit blood circulation in the tail.

Hindlimb unloading leads to rapid loss of muscle mass in hindlimb muscles such as the soleus and to demineralization of hindlimb bones. When young, growing animals are used, the rate of growth is slowed, whereas when adult animals are used, there is a loss of body weight during the first few days of the experiment.

Thirty-two adult male Sprague-Dawley rats (mean weight=387 grams) are randomly assigned to four groups as follows: 1) a saline control group, which is injected with saline but not suspended; 2) a saline suspended group, which is injected with saline and is suspended; 3) a control group, which is injected with a compound of this invention, but were not suspended; and 4) a suspended group, which is injected with a compound of this invention and is suspended.

Body weight and food consumption measurements are begun two days prior to suspension (day 0) and are made every day thereafter throughout the treatment period. As compared to control rats, which receive saline, administration of a compound of this invention reduces the loss of body weight due to hindlimb suspension. A reduction in the rate of loss of body weight may be evident by the second day of treatment with the compound of this invention and the reduction in weight loss of the animals treated with a compound of this invention as compared to the control animals is maintained throughout the treatment period.

At the end of the treatment period, the rats are sacrificed and various tissues and organs are removed and weighed. Administration of a compound of this invention significantly reduces the weight of the fat pads in both the unsuspended and suspended groups as compared to the saline controls. Administration of a compound of this invention also attenuates the loss of organ weight and muscle mass, with particular benefit observed in the soleus muscle and the heart.

The present invention is illustrated by the following Examples. However, it should be understood that the invention is not limited to the specific details of these Examples.

Example One

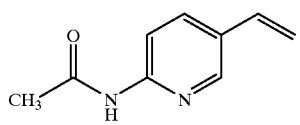

N-(5-Vinyl-pyridin-2-yl)-acetamide.

A solution of of N-(5-bromo-pyridin-2-yl)-acetamide (4.30 g, 20 mmol) in acetonitrile (15 ml) and triethylamine (5.04 ml) was treated with palladium acetate (45 mg, 0.2 mmol) and tri-o-tolylphosphine (203 mg, 0.66 mmol). The mixture was placed in a pressure reactor under 50 psig of ethylene pressure and heated at 85° C. for 66 hours. The reaction mixture was cooled, vented, and partitioned between phosphate buffer (0.1 M, pH 6.6) and ethyl acetate. The aqueous phase was extracted with ethyl acetate twice more. The combined ethyl acetate extracts were washed with additional phosphate buffer, brine and dried over sodium sulfate. The extracts were filtered and evaporated to afford 2.06 g (63%) of the title product as a flaky crystalline residue. Recrystallization from ethyl acetate/cyclohexane gave colorless flakes. mp 120–121° C. 1H NMR (CDCl$_3$): δ=8.55 (br, 1 H); 8.24 (d, 1 H); 8.15 (d, 1 H); 7.76 (d of d, 1H); 6.64 (d of d, 1 H); 5.73 (d, 1 H); 5.28 (d, 1 H); 2.19 (s, 3 H). MS (Cl): m/z=163 (M+H$^+$).

Example Two

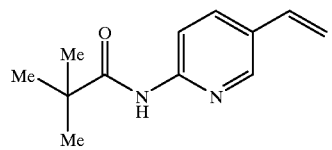

N-(5-Vinyl-pyridin-2-yl)-2,2-dimethylpropionamide.

A solution of N-(5-bromopyridin-2-yl)-2,2-dimethylpropionamide (5.60 g, 21.8 mmol) in acetonitrile (20 ml) and triethylamine (5.49 ml) was treated with palladium acetate (177 mg, 0.8 mmol) and tri-o-tolylphosphine (795 mg, 2.6 mmol). The mixture was placed in a pressure reactor under 130 psig of ethylene pressure and heated at 85° C. for 18 hours. The reaction mixture was cooled, vented, diluted with ethyl acetate and filtered. The ethyl acetate solution was washed sequentially with dilute citric acid, water and brine and then dried over sodium sulfate. The dried solution was filtered and evaporated. Chromatography of the residue on silica gel, eluting with dichloromethane/ethyl acetate (24:1) afforded 3.92 g (88%) of the title product as an oil. $^1$H NMR (CDCl$_3$): δ=8.21 (m, 2 H); 8.03 (br, 1 H); 7.76 (d of d, 1 H); 6.63 (d of d, 1 H); 5.71 (d, 1 H); 5.25 (d, 1 H); 1.29 (s, 9H). MS (Cl): m/z=205 (M+H$^+$).

Example Three

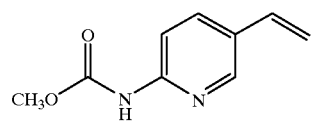

N-(5-Vinyl-pyridin-2-yl)-carbamic acid methyl ester.

A solution of (5-bromo-pyridin-2-yl)-carbamic acid methyl ester (1.68 g, 7.2 mmol) in acetonitrile (15 ml) and triethylamine (1.84 ml) was treated with palladium acetate (65 mg, 0.29 mmol) and tri-o-tolylphosphine (295 mg, 0.97 mmol). The mixture was placed in a pressure reactor under 130 psig of ethylene pressure and heated at 85° C. for 18 hours. The reaction mixture was cooled, vented and diluted with ethyl acetate and filtered. The ethyl acetate solution was washed sequentially with 1M aqueous citric acid, water, brine and was dried over sodium sulfate and filtered. The filtrate was evaporated. The residue was recrystallized from dichloromethane-hexane to afford 0.759 g (58%) of the title product as colorless crystals. mp 146–148° C. $^1$H NMR (CDCl$_3$): δ=9.04 (br, 1 H); 8.28 (d, 1 H); 7.97 (d, 1 H); 7.77 (d of d, 1 H); 6.64 (d of d, 1 H); 5.71 (d, 1 H); 5.26 (d, 1 H); 3.81 (s, 3H). MS (Cl): m/z =179 (M+H$^+$).

Example Five

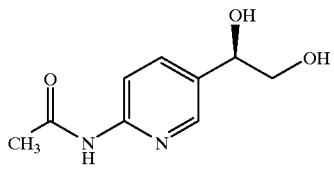

(R)-N-(5-(1.2-Dihydroxy-ethyl)-pyridin-2-yl)-acetamide.

A suspension of AD-Mix-B® (56.33 g) in water (200 ml) and t-butanol (200 ml) was cooled to 5° C. and N-(5-Vinyl-pyridin-2-yl)-acetamide (6.52 g, 40.2 mmol) was added followed by 2-propanol (400 ml). The mixture was stirred at 5° C. for 12 hours and then at 20 ° C. for 12 hours. The reaction mixture was then treated with sodium sulfite (60.4 g), stirred for 30 minutes and then diluted with 500 ml of 2-propanol and stirred for an additional one hour. The mixture was filtered and the alcoholic phase was separated and evaporated to dryness. The residue was slurried in 500 ml of 2-propanol and evaporated again. The residue was dried to afford 6.35 g (80%) of the title product as colorless crystals. The crystals were recrystallized by dissolving in hot glacial acetic acid, diluting 7-fold with 2-propanol, cooling and seeding to give the title product as crystals. mp 184–185° C. $^1$H NMR (dmso-d$_6$): δ=8.22 (d, 1 H); 7.99 (d, 1 H); 7.68 (d of d, 1 H); 4.52 (t, 1 H); 3.44 (m, 2 H); 2.07 (s, 3 H). MS (Cl): m/z=197 (M+H$^+$). Optical Rotation: –4.52° (c=0.05, acetic acid). Analysis: Calculated for $C_9H_{12}N_2O_3$: C, 55.09%; H, 6.17%; N, 14.28%. Found: C, 55.43%; H, 5.97%; N, 13.96%.

Example Six

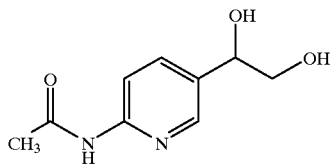

(R,S)—N—(5-(1.2-Dihydroxy-ethyl)-pyridin-2-yl)-acetamide.

A vigorously stirred mixture of potassium carbonate (25.56 g, 185 mmol), potassium ferricyanide (60.9 g, 185 mmol) and N-(vinyl-pyridin-2-yl)-acetamide (100.0 g, 61.6 mmol) in water (120 ml) and 2-propanol (120 ml) was treated with potassium osmate (VI) dihydrate (46 mg, 0.123 mmol) at 25° C. The mixture was then stirred for one hour. The mixture was separated and the aqueous phase was extracted three times more with 120 ml portions of 2-propanol. The residue from the aqueous phase was triturated with hot 2-propanol. The 2-propanol extracts were combined, concentrated and azeotropically dried with 2-propanol. The residue was triturated with ether, filtered, washed with ether and dried to afford 10.61 g (87%) of the title product as an off white solid. mp 160–162° C. $^1$H NMR (dmso-d$_6$): δ=8.22 (d, 1 H); 7.99 (d, 1 H); 768 (d of d, 1 H); 4.52 (t, 1 H); 3.44 (m, 2 H); 2.07 (s, 3 H). MS (Cl): m/z=197 (M+H$^+$).

Example Seven

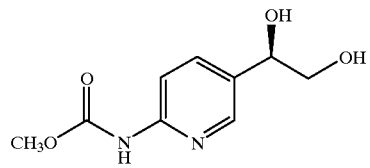

(R)-N-(5-('1 2-(Di hyd roxy-ethyl )-pyrd in-2-yl)-carbamic acid methyl ester.

A suspension of AD-Mix-B® (2.80 g) in water (10 ml) and t-butanol (10 ml) was cooled to 5° C. and N-(5-vinyl-pyridin-2-yl)-carbamic acid methyl ester (0.356 g, 2.0 mmol) was added. The mixture was stirred at 5° C. for 18 hours. The reaction mixture was then treated with sodium sulfite (3.0 g), stirred for an additional 30 minutes and then extracted three times with ethyl acetate. The ethyl acetate extracts were combined and washed with water and brine and dried and evaporated to afford 0.410 g (96%) of the title product as colorless crystals. mp 153–154° C. $^1$H NMR (CDCl$_3$): δ=8.90 (br, 1 H); 8.09 (d, 1 H); 7.75 (d, 1 H); 7.53 (d of d, 1 H); 4.55 (m, 1 H); 3.60 (s, 3 H); 3.47 (m, 1 H); 3.41 (m, 1 H). MS (Cl): m/z=213 (M+H$^+$).

Example Eight

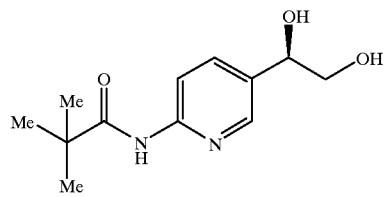

(R)-N-(5-(1.2-Dihydroxy-ethyl)-pyrdin-2-yl)-2,2-dimethylpropionamide.

A suspension of AD-Mix-B® (1.40 9) in water (5 ml) and t-butanol (5 ml) was cooled to 5° C. and N-(5-vinyl-pyridin-2-yl)-2,2-dimethylpropionamide (0.204 g, 1.0 mmol) was added. The mixture was stirred at 5° C. for 18 hours. The reaction mixture was then treated with sodium sulfite (3.0 g), stirred for 30 minutes and then extracted with dichloromethane.

The dichloromethane extract was washed with water and brine and then dried and evaporated to afford 0.230 g (96%) of the title product as colorless crystals. mp 105–106° C. $^1$H NMR (CDCl$_3$): δ=8.21 (br, 1 H); 8.10 (m, 2 H); 7.61 (d of d, 1 H); 4.70 (m, 1 H); 3.64 (m, H); 3.57 (m, 1 H); 1.25 (s, 9 H). MS (Cl): m/z=239 (M+H$^+$).

Example Nine

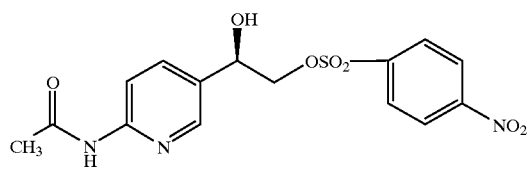

(R)-4-Nitro-benzenesulfonic acid 2-(6-acetylamino-pyridin-3-yl)-2-hydroxy-ethyl ester.

A solution of (R)-(5-(1,2-dihydroxy-ethyl)-pyridin-2-yl)-acetamide (0.294, 1.5 mmol) in anhydrous DMF (3 ml) was treated with triethylamine (0.63 g, 4.5 mmol) and cooled to −40° C. A solution of 4-nitrobenzenesulfonyl chloride (0.332 g, 1.5 mmol) in ethyl acetate (3 ml) was added dropwise. After 45 minutes at −45° C., the mixture was stirred for one hour at 20° C. The mixture was then diluted with ethyl acetate and washed sequentially with water, twice with pH 6.6 buffer (0.1 M phosphate), water and brine. The ethyl acetate layer was dried over sodium sulfate, filtered and evaporated. The residue was triturated with 1,2-dichloroethane to give 0.381 g (67%) of the title product as colorless crystals. mp 116–120° C. with decomposition. $^1$H NMR (dmso-d$_6$): δ=8.36 (d, 2 H); 8.16 (d, 1 H); 8.04 (d, 2 H); 7.91 (d, 1 H); 7.62 (d of d, 1 H); 5.89 (d, 1 H); 4.81 (d of d, 1 H); 4.24 (d, 2 H); 2.06 (s, 3 H). MS (Cl): m/z=179 (M+H$^+$O$_2$NC$_6$H$_4$SO$_3$H).

Example Ten

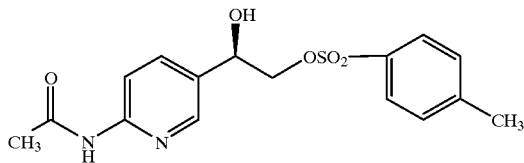

(R)-Toluene-4-sulfonic acid 2-(6-acetylamino-pyridin-3-yl)-2-hydroxy-ethyl ester. A slurry of (R)-N-(5-(1,2-dihydroxy-ethyl)-pyridin-2-yl)-acetamide (71.2 g, 362 mmol) in anhydrous pyridine (362 ml) was cooled to 5° C. and treated with p-toluenesulfonyl chloride (69.18 g, 362 mmol) in one portion. The reaction mixture was stirred at 5° C. for 20 minutes, then the cooling bath was removed and the mixture was stirred at ambient temperature for two hours. The mixture was then concentrated, dissolved in 30 ml of methanol, concentrated and dissolved in toluene (300 ml) and concentrated again. The residue was treated again with methanol and toluene, then the residue was dissolved in ethyl acetate and washed sequentially with half-saturated brine, brine and dried over sodium sulfate. The filtrate was evaporated to afford 102.2 g (80%) of the title product as light buff crystals. Recrystallization from ethanol-cyclohexane afforded the title product as colorless crystals. mp 124–126° C. $^1$H NMR (dmso-d$_6$): δ=10.5 (br, 1 H); 8.21 (d, 1 H); 7.94 (d, 1 H); 7.68 (d, 2 H); 7.51 (d of d, 1 H); 7.41 (d, 1 H); 5.87 (d, 1 H); 4.76 (d of d, 1 H); 4.05 (d, 2 H); 2.41 (s, 3 H); 2.10 (s, 3 H). MS (Cl): m/z=351 (M+H$^+$). Optical Rotation: −36.181° (c=1.19, acetone). Analysis: Calculated for C$_{16}$H$_{18}$N$_2$O$_5$S: C, 54.85%; H, 5.18%; N, 7.99%. Found: C, 54.91%; H, 5.34%; N, 8.06%.

Example Eleven

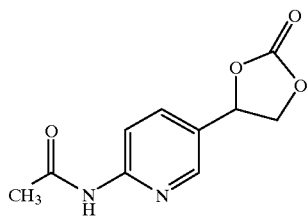

N-(5-(2-Oxo-[1.3]dioxolan-4-yl)-pyridin-2-yl)-acetamide.

A solution of (R,S)-N-(5-(1,2-dihydroxy-ethyl-pyridin-2-yl)-acetamide (0.392 g, 2 mmol) and 1,1'-carbonyldiimidazole (0.648 g, 4 mmol) in DMF (3 ml) was stirred at 20° C. for six hours and then concentrated under high vacuum. The residue was treated with water and ethyl acetate. The ethyl acetate was separated and the aqueous phase was extracted three additional times with ethyl acetate. The combined ethyl acetate extracts were washed with brine, dried, filtered and concentrated. Chromatography of the residue on silica gel, eluting with dichloromethane/methanol (1:1) afforded 0.078 g (17%) of the title product as white crystals. mp 135–139° C. $^1$H NMR (dmso-d$_6$): δ=8.41 (d, 1 H); 8.11 (d, 1 H); 7.93 (d of d, 1 H); 5.85 (t, 1 H); 4.84 (t, 1 H); 4.47 (t, 1 H); 2.09 (s, 3 H). MS (Cl): m/z=223 (M+H$^+$).

Example Twelve

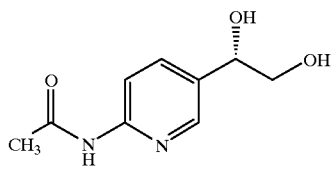

(S)-N-(5-(1 2-Dihydroxy-ethyl)-pyridin-2-yl)-acetamide.

A suspension of AD-Mix-α® (35 g) in water (50 ml) and 2-propanol (50 ml) was cooled to 0° C. and N-(5-Vinyl-pyridin-2-yl)-acetamide (4.05 g, 25 mmol) was added. The mixture was stirred overnight at 20° C. The reaction mixture was then treated with sodium sulfite (37.5 g). The 2-propanol was decanted. The residue was diluted with 2-propanol (50 ml) and refluxed and the 2-propanol was decanted. This process was repeated three times. The alcoholic portions were combined, filtered and the filtrate was concentrated to afford a yellow solid. This solid was reslurried in hot 2-propanol (20 ml) and filtered to afford 3.80 g of impure product. This was dissolved in hot ethyl acetate (6 ml). Acetonitrile (42 ml) was added. The solution was cooled to precipitate the product. The suspension was stirred overnight and filtered to afford 3.0 g (61%) of an off-white solid. $^1$H NMR (dmso-d$_6$): δ=8.22 (d, 1 H); 7.99 (d, 1 H); 7.68 (d of d, 1 H); 4.52 (t, 1 H); 3.44 (m, 2 H); 2.07 (s, 3 H). ms (Cl): m/z=197 (M+H$^+$).

Example Thirteen

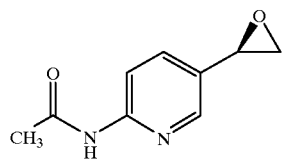

(R)-N-(5-Oxiranyl-pyridin-2-yl)-acetamide.

A solution of (R)-toluene-4-sulfonic acid 2-(6-acetylamino-pyridin-3-yl)-2-hydroxy-ethyl ester (200 g, 0.57 mol) in THF (2.4 L) was cooled to −15° C. and potassium t-butoxide (542 ml, 0.542 mol, 1M in THF) was added slowly at −15° C. to −10° C. over a two hour period. Stirring was continued at −15° C. for an additional 40 minutes. The reaction mixture was filtered with the aid of Celite®. The filtration was done through cloth precoated with Celite®. The filter cake was washed with tetrahydrofuran. The filtrate was concentrated under vacuum to afford 300 ml of an oil. The oil was diluted with 1.2 liters of hexanes which resulted in the formation of a solid. The suspension was stirred at room temperature for one hour to granulate the solid. The suspension was filtered and the filtrate was washed with hexanes to afford 80.0 g (78.8%) of the title product as a solid. mp 96–98° C. $^1$H NMR (CDCl$_3$):

δ=8.70 (br, 1 H); 8.21 (m, 2 H); 7.57 (d of d, 1 H); 3.86 (m, 1 H); 3.17 (m, 1 H); 2.83 (m, 1 H); 2.19 (s, 3 H). MS (Cl): m/z=179 (M+H$^+$).

Example Fourteen

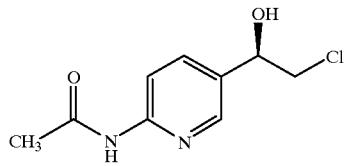

(R)-N-(5-(2-Chloro-1-hydroxy-ethyl)-pyridin-2-yl)-acetamide.

A mixture of (R)-N-(5-(2-chloro-1-hydroxy-ethyl)-pyridin-2-yl)-acetamide and (R)-toluene-4-sulfonic acid 2-(6-acetylamino-pyridin-3-yl)-2-hydroxy-ethyl ester (86.3 g) was dissolved in 604 ml of ethanol. The solution was heated to obtain a clear solution and then lithium chloride (10.3 g, 0.243 mol) was added. The reaction mixture was heated under reflux overnight. Additional lithium chloride (2.0 g) was added and the reaction was heated under reflux for an additional two days. The reaction mixture was cooled and concentrated in vacuum. The residue was partitioned between ethyl acetate and half-saturated brine. The layers were separated and the ethyl acetate layer was washed once with saturated brine. The aqueous layers were combined and extracted once with ethyl acetate. The ethyl acetate layers were combined and dried with MgSO$_4$ then concentrated to an oil. The residue was dissolved in tetrahydrofuran to obtain a hazy solution. This solution was treated with charcoal and silica gel, stirred warm for 30 minutes and filtered. The filter cake was washed with tetrahydrofuran and the solution was concentrated to a semi-solid. The semi-solid was dissolved in 500 ml of ethyl acetate, washed with half-saturated brine, once with saturated aqueous sodium bicarbonate and once with saturated aqueous sodium chloride. The ethyl acetate layer was concentrated to afford an oil. The resulting suspension was slurried in methylene chloride (100 ml), cooled then vacuum filtered to afford 29 g of title chloride compound. $^1$H NMR (DMSO-d$_6$): δ=10.48 (br s, 1H); 8.29 (d, 1H); 8.00 (d, 1H); 7.73 (d of d, 1H); 5.88 (d, 1H); 4.76 (m, 1H); 3.72 (m, 1H); 2 .06 (s, 3H).

Example Fifteen

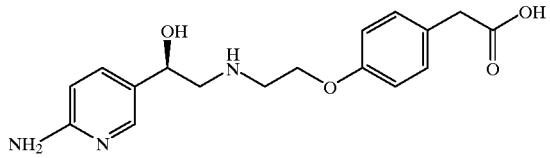

(4-(2-(2-(6-Aminopyridin-3-yl)-2-(R)-hydroxyethylammonium)-ethoxy)-phenyl)-acetate.

A mechanically stirred slurry of the title compound of Example Thirteen (50.0 gm, 0.2806 mol, 1.0 eq) and the title compound of Preparation Seven (99.4 gm, 0.477 mol, 1.7eq) in 5:1 (vol/vol)::Toluene:DMSO (375 mL) was heated on a steam bath. The slurry became homogenous at about 70° C., and the temperature was maintained at 90–95° C. for 3 to 16 hrs. The solution was cooled to 10–15°. This resulted in the formation of a precipitate. Di-t-butyldicarbonate (129 mL, 0.561 mol, 2.0 eq) was added dropwise over a one hour period. The resulting homogenous solution was stirred at room temperature overnight. The solution was poured into a mixture of ethyl acetate (1 L) and water (850 mL). After stirring for 10 min, the phases were allowed to separate, at which time a heavy red oil fell out into the aqueous layer. The aqueous layer, with oil, was removed. The organic layer was washed with water (500 mL) and concentrated to an amber oil. This amber oil was taken up in 6N HCl (300 mL) and heated on the steam bath overnight. The solution was cooled to room temperature, and the solids which precipitated were filtered. (These solids are the amino acid of the excess side chain which was used in the coupling with the epoxide.) The acidic solution containing the title compound was concentrated under vacuum to a semi-solid. The semi-solid was treated with water and then reconcentrated (twice) to remove excess HCl. The solid was dissolved in water and brought to pH 7 with potassium hydroxide. The solid which precipitated was filtered and washed first with water and then with THF. The solids were dried on the filter funnel to a weight of 22.5 gm. The crude solid was redissolved in 30 volumes of 90° C. water and treated with decolorizing carbon. After filtration to remove the carbon, the filtrate was cooled and concentrated by evaporation of some of the water. The precipitate which formed was filtered to provide 9.5 gm of the title compound. NMR (400 MHz, DMSO-d$_6$+D$_2$O): d=7.79 (d, 1H, J=1.87), 7.34–7.32 (m, 1H), 7.11 (d, 2H, J=8.51), 6.79 (d, 2H, J=8.51), 6.41 (d, 1H, J=8.51), 4.54–4.51 (m, 1H), 401 –3.99 (m, 2H), 3.35 (s, 2H), 2.97–2.94 (m, 2H), 2.79–2.69 (m, 2H). MS (APCl) m/z 332.2 (MH$^+$), 314.2, 159.1, 156.9.

Preparation One

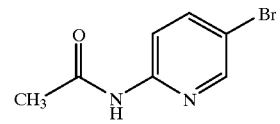

N-(5-Bromo-pyridin-2-yl)-acetamide.

A solution of 2-amino-5-bromopyridine (25.0 g, 144 mmol) in acetic acid (50 ml) and acetic (25.0 g, anhydride (250 ml) was heated at reflux for two hours. The reaction mixture was then cooled and poured into water (750 ml) with stirring. After one hour, the solution was adjusted to pH 10 with 50% sodium hydroxide and the precipitate was filtered, washed with water and dried to give 26.5 g (85%) of the title product as a white flaky solid. mp 175–176° C. $^1$H NMR (CDCl$_3$): δ=8.29 (d, 1 H); 8.12 (d, 1 H); 7.96 (br, 1 H); 7.78 (d of d, 1 H); 2.19 (s, 3 H). MS (El): m/z=214, 216 (M$^+$, Br isotopes).

Preparation Two

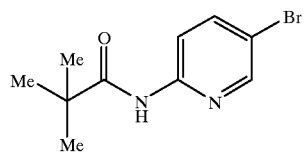

N-(5-Bromo-pyridin-2-yl)-2,2-dimethylpropionamide.

A solution of trimethylacetyl chloride (17.5 g, 146 mmol) in dichloromethane (25 ml) was added to a solution of 2-amino-5-bromopyridine (25.0 g, 144 mmol) in dichloromethane (100 ml) and triethylamine (24 ml) dropwise with stirring at 20° C. The reaction mixture was then stirred for 40 minutes, filtered, washed with water, dried and concentrated. Recrystallization from hexanes afforded 20.6 g (70%) of the title product as a white flaky solid. mp 63–64° C. $^1$H NMR (CDCl$_3$): δ=8.82 (br, 1 H); 8.30 (d, 1 H); 8.19 (m, 2 H); 1.36 (s, 3 H). MS (El): m/z=256, 258 (M$^+$, Br isotopes).

Preparation Three

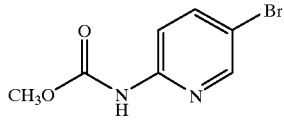

N-(5-Bromo-pyridin-2-yl)-carbamic acid methyl ester.

A solution of 2-amino-5-bromopyridine (9.46 g, 20 mmol) and N,N-diisopropylethylamine (3.10 g) in chloroform (20 ml) was added to a solution of methyl chloroformate (2.30 g, 24 mmol) in chloroform (25 ml) dropwise with stirring at 0° C. The reaction mixture was stirred for 20 minutes, filtered and the precipitate was washed with chloroform and dried to afford 1.71 g (37%) of the title product as a white solid. mp 191–192° C. $^1$H NMR (CDCl$_3$): δ=8.42 (d, 1 H); 8.30 (d, 1 H); 7.91 (d, 1 H); 7.77 (d of d, 1 H); 3.79 (s, 3 H). MS (El): m/z=230, 232 (M$^+$, Br isotopes).

Preparation Four

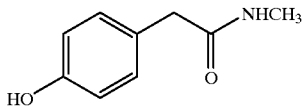

N-Methyl 4-hydroxyphenylacetamide. Monomethylamine (22.43 kg, 722.15 mol, 6 eq.) was added over a 7-hour period to a solution of methyl-4-hydroxyphenylacetate (20.0 kg, 120.35 mol, 1.0 eq.) in methanol (31.7 gal) and stirred overnight at room temperature. Methanol was then displaced under vacuum with ethyl acetate. The resulting slurry (ca. 20 gal) was stirred at +10° C. for 1 hour, then filtered and dried under vacuum at 45° C. to yield of the title compound(1 8.68 kg, 94% of theory). mp 124–125° C. NMR (300 MHz, d$_6$-DMSO): δ=9.26 (s, 1H), 8.00–7.65 (br s, 1H), 7.21–6.90 (m, 2H), 6.86–6.55 (m, 2H), 3.26 (s, 2H), 2.75–2.45 (m, 3H).

Preparation Five

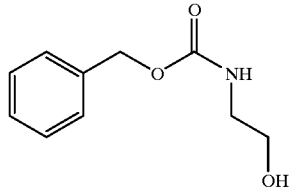

N-Benzyloxycarbonyl-2-aminoethanol.

Benzylchloroformate (44.95 kg, 263.5 mol, 1.0 eq.) was added over a 2 hour period at room temperature to a solution of ethanolamine (16.1 kg, 263.5 mol, 1.0 eq.) in water (34 gal). After stirring for 30 minutes, this was added to a cold (5–10° C.) solution of NaHCO$_3$ (33.2 kg, 395.25 mol, 1.5 eq) in H$_2$O (330 L) over a 30 min period and then allowed to stir at room temperature overnight. Ethyl acetate (22 gal) was added, the layers separated, and the aqueous layer extracted again with 22 gal. ethyl acetate. The combined organic extracts were concentrated under vacuum to a volume of 10 gal, and the remainder displaced with isopropyl ether. The resulting slurry was stirred and cooled to +10° C. for 2 hours, then filtered. The solids were washed with isopropyl ether and vacuum dried to give the title compound (39.1 kg, 71.1%). mp 61–63° C. NMR (300 MHz, d$_6$-DMSO): δ=7.50–7.37 (m, 5H), 7.37–7.16 (m, 1H), 5.05 (s, 2H), 4.70–4.63 (m, 1H), 3.46–3.37 (m, 2H), 3.13–3.03 (m, 2H).

Preparation Six

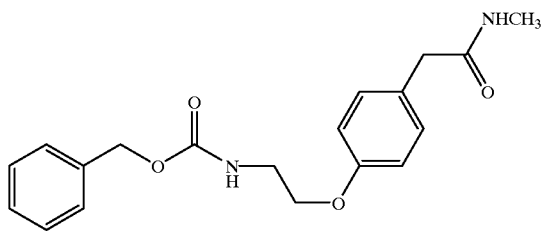

Methyl 4-(2-(N-benzyloxycarbonylamino)ethoxy) phenylacetamide.

The title compound of Preparation Four (18.68 kg, 113.14 mol, 1.0 eq.) and the title compound of Preparation Five (33.13 kg, 169.75 mol, 1.5 eq.) were dissolved in THF (40 gal). Triphenylphosphine (44.5 kg, 169.75 mol, 1.5 eq.) was added and the mixture cooled to −5° C. Diisopropyl azodicarboxylate (34.3 kg, 169.75 mol, 1.5 eq.) was added over an 8 hour period, and the reaction allowed to warm to room temperature overnight. Ethyl acetate (20 gal) was added to the resulting white slurry, stirring was continued for 6 hours, and the solids filtered off and dried to yield crude title compound. (29.6 kg, 76.5% of theory, mp 131–133° C.). The crude product was slurried in ethyl acetate (39.1 gal) for 3 hours at +10° C., then filtered, washed with 14 gal 10° C. ethyl acetate, and vacuum dried to yield the title compound (26.1 kg, 88.2 % recovery, 67.5% overall). mp 134–136° C. NMR (300 MHz, d$_6$-DMSO): δ=7.98–7.82 (m, 1H), 7.58–7.49 (m, 1H), 7.42–7.28 (m, 5H), 7.20–7.10 (d, 2H), 6.90–6.80 (d, 2H), 5.06 (s, 2H), 4.02–3.93 (m, 2H), 3.47–3.29 (m, 4H), 2.62–2.54 (d, 3H).

Preparation Seven

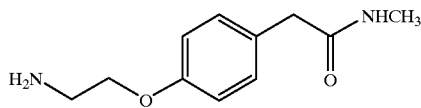

Methyl 4-(2-aminoethoxy)phenylacetamide.

The title compound of Preparation Six (18.4 kg, 53.73 mol) and 1.84 kg 10% palladium on carbon (50% H$_2$O wet) were suspended in 73 gal methanol under nitrogen, and the reaction vessel pressurized to 50 psig with hydrogen gas. This H$_2$ pressure was maintained by additional charges of H$_2$ until there was no further uptake of H$_2$ (approx. 20 hours) and the reaction was complete by tlc. After purging the vessel with N$_2$, the mixture was heated to 45° C. and filtered at this temperature through Celite. The solvent was displaced with toluene until a final volume of 8 gal was achieved. After cooling to +5° C. the resulting solids were filtered off, washed with cold toluene, and vacuum dried to give the title compound (9.95 kg, 88.9% of theory). NMR (300 MHz, d$_6$-DMSO): δ=7.99–7.57 (m, 1H), 7.20–7.10 (d, 2H), 6.90–6.80 (d, 2H), 3.93–3.83 (m, 2H), 3.30 (s, 2(m, 4H), 2.57 (d, 2H).

It is claimed:

1. A method of reducing a wasting condition in a mammal, comprising administering to a mammal having a wasting condition a therapeutically effective amount of (4-(2-(2-(6-Aminopyridin-3-yl)-2(R)-hydroxyethylamino)ethoxy) phenyl)acetic acid; (4-(2-(2-(6-Aminopyridin-3-yl)-2(R)-hydroxyethylamino)ethoxy)phenoxy)acetic acid; 4-(2-(2-(6-Aminopyridin-3-yl)-2(R)-hydroxyethylamino)ethoxy) benzoic acid; or (4-(2-(2-(6-Aminopyridin-3-yl)-2(R)-hydroxyethylamino)ethoxy)phenyl)propionic acid; or a pharmaceutically acceptable salt of any of said compounds.

2. The method of claim 1 wherein the wasting condition is muscle wasting.

3. The method of claim 1 wherein said wasting condition is due to a pathology.

4. The method of claim 1 wherein said wasting condition is due to disuse deconditioning.

5. The method of claim 1 wherein said wasting condition is due to muscle denervation.

6. The method as recited in claim 2 wherein the Formula I compound is (4-(2-(2-(6-Aminopyridin-3-yl)-2(R)-hydroxyethylamino)ethoxy)phenyl)acetic acid.

7. The method as recited in claim 2 wherein the Formula I compound is (4-(2-(2-(6-Aminopyridin-3-yl)-2(R)-hydroxyethylamino)ethoxy)phenoxy)acetic acid.

8. The method as recited in claim 2 wherein the Formula I compound is 4-(2-(2-(6-Aminopyridin-3-yl)-2(R)-hydroxyethylamino)ethoxy)benzoic acid.

9. The method as recited in claim 2 wherein the Formula I compound is (4-(2-(2-(6-Aminopyridin-3-yl)-2(R)-hydroxyethylamino)ethoxy)phenyl)propionic acid.

10. A method of reducing a wasting condition in a mammal comprising administering a pharmaceutical composition comprising a therapeutically effective amount of (4-(2-(2-(6-Aminopyridin-3-yl)-2(R)-hydroxyethylamino) ethoxy)phenyl)acetic acid; (4-(2-(2-(6-Aminopyridin-3-yl)-2(R)-hydroxyethylamino) ethoxy)phenoxy)acetic acid; 4-(2-(2-(6-Aminopyridin-3-yl)-2(R)-hydroxyethylamino)ethoxy)benzoic acid; or (4-(2-(2-(6-Aminopyridin-3-yl)-2(R)-hydroxyethylamino) ethoxy)phenyl)propionic acid; or the pharmaceutically acceptable salt of any of said compounds and a pharmaceutically acceptable carrier to the mammal.

11. The method of claim 10 wherein the wasting condition is muscle wasting.

12. The method of claim 10 wherein said wasting condition is due to a pathology.

13. The method of claim 10 wherein said wasting condition is due to disuse deconditioning.

14. The method of claim 10 wherein said wasting condition is due to muscle denervation.

15. The method as recited in claim 11 wherein the Formula I compound is (4-(2-(2-(6-Aminopyridin-3-yl)-2 (R)-hydroxyethylamino)ethoxy)phenyl)acetic acid.

16. The method as recited in claim 11 wherein the Formula I compound is (4-(2-(2-(6-Aminopyridin-3-yl)-2 (R)-hydroxyethylamino)ethoxy)phenoxy)acetic acid.

17. The method as recited in claim 11 wherein the Formula I compound is 4-(2-(2-(6-Aminopyridin-3-yl)-2 (R)-hydroxyethylamino)ethoxy)benzoic acid.

18. The method as recited in claim 11 wherein the Formula I compound is (4-(2-(2-(6-Aminopyridin-3-yl)-2 (R)-hydroxyethylamino)ethoxy)phenyl)propionic acid.

* * * * *